(12) United States Patent
Reddy et al.

(10) Patent No.: US 7,308,297 B2
(45) Date of Patent: Dec. 11, 2007

(54) CARDIAC IMAGING SYSTEM AND METHOD FOR QUANTIFICATION OF DESYNCHRONY OF VENTRICLES FOR BIVENTRICULAR PACING

(75) Inventors: Shankara Bonthu Reddy, Windham, NH (US); Maggie Mei-Kei Fung, Waukesha, WI (US); Jasbir S. Sra, W. 305 N. 2963 Red Oak Ct., Pewaukee, WI (US) 53072; Darrin R. Okerlund, Muskego, WI (US); Christine Mary Palmer, Plover, WI (US)

(73) Assignees: GE Medical Systems Global Technology Company, LLC, Waukesha, WI (US); Jasbir S. Sra, Pewaukee, WI (US)

( * ) Notice: Subject to any disclaimer, the term of this patent is extended or adjusted under 35 U.S.C. 154(b) by 716 days.

(21) Appl. No.: 10/605,903

(22) Filed: Nov. 5, 2003

(65) Prior Publication Data

US 2005/0096522 A1   May 5, 2005

(51) Int. Cl.
*A61B 5/05* (2006.01)
(52) U.S. Cl. ............................ 600/407; 600/425; 378/4
(58) Field of Classification Search ................. 600/407
See application file for complete search history.

(56) References Cited

U.S. PATENT DOCUMENTS

| | | | |
|---|---|---|---|
| 3,954,098 A | 5/1976 | Dick et al. ................. 600/440 |
| 4,364,397 A | 12/1982 | Citron et al. | |
| 4,574,807 A | 3/1986 | Hewson et al. ........ 128/419 PG |
| 5,245,287 A | 9/1993 | Nowak et al. .............. 324/322 |
| 5,274,551 A | 12/1993 | Corby, Jr. .............. 364/413.13 |
| 5,304,212 A | 4/1994 | Czeisler et al. ............... 607/88 |
| 5,348,020 A | 9/1994 | Huston ....................... 128/696 |
| 5,353,795 A | 10/1994 | Souza et al. ............. 128/653.2 |
| 5,391,199 A | 2/1995 | Ben-Haim .................. 607/122 |
| 5,431,688 A | 7/1995 | Freeman ..................... 607/10 |
| 5,515,849 A * | 5/1996 | Murashita et al. .......... 600/479 |

(Continued)

FOREIGN PATENT DOCUMENTS

EP          1182619 A2      2/2002

(Continued)

OTHER PUBLICATIONS

Gerard et al. Efficient Model-Based Quantification of Left Ventricular Function in 3-D Echocardiography. IEEE Transactions on Medical Imaging. 21(9): pp. 1059-1068. Sep. 2002.*

(Continued)

*Primary Examiner*—Brian L. Casler
*Assistant Examiner*—Parikha S. Mehta
(74) *Attorney, Agent, or Firm*—Cantor Colburn LLP

(57) ABSTRACT

A method for quantifying cardiac desynchrony of the right and left ventricles includes obtaining cardiac acquisition data from a medical imaging system, and determining a movement profile from the cardiac acquisition data. The movement profile is directed toward identifying at least one of a time-based contraction parameter for a region of the left ventricle (LV), and a displacement-based contraction parameter for a region of the LV. The determined movement profile is visually displayed by generating a 3D model therefrom.

68 Claims, 10 Drawing Sheets

U.S. PATENT DOCUMENTS

| | | | | |
|---|---|---|---|---|
| 5,568,384 | A | 10/1996 | Robb et al. | 364/419.13 |
| 5,738,093 | A | 4/1998 | Ben-Haim | 128/653.1 |
| 5,765,561 | A | 6/1998 | Chen et al. | |
| 5,823,958 | A | 10/1998 | Truppe | 600/426 |
| 5,839,440 | A | 11/1998 | Liou et al. | 128/654 |
| 5,951,475 | A | 9/1999 | Gueziec et al. | 600/425 |
| 6,058,218 | A * | 5/2000 | Cline | 382/254 |
| 6,081,577 | A | 6/2000 | Webber | 378/23 |
| 6,154,516 | A | 11/2000 | Heuscher et al. | 378/15 |
| 6,208,347 | B1 | 3/2001 | Migdal | 345/419 |
| 6,233,304 | B1 | 5/2001 | Hu et al. | 378/8 |
| 6,235,038 | B1 | 5/2001 | Hunter et al. | 606/130 |
| 6,235,083 | B1 | 5/2001 | Hunter et al. | 606/130 |
| 6,246,898 | B1 * | 6/2001 | Vesely et al. | 600/424 |
| 6,249,693 | B1 | 6/2001 | Cline et al. | 600/410 |
| 6,252,924 | B1 | 6/2001 | Davantes et al. | 378/8 |
| 6,256,368 | B1 | 7/2001 | Hsieh et al. | 378/8 |
| 6,266,553 | B1 | 7/2001 | Fluhrer et al. | 600/428 |
| 6,289,115 | B1 | 9/2001 | Takeo | 382/130 |
| 6,289,239 | B1 | 9/2001 | Panescu et al. | 600/523 |
| 6,314,310 | B1 | 11/2001 | Ben-Haim et al. | 600/424 |
| 6,325,797 | B1 | 12/2001 | Stewart et al. | 606/41 |
| 6,348,793 | B1 | 2/2002 | Balloni et al. | 324/309 |
| 6,353,445 | B1 | 3/2002 | Babula et al. | 345/733 |
| 6,381,485 | B1 | 4/2002 | Hunter et al. | 600/407 |
| 6,389,104 | B1 | 5/2002 | Bani-Hashemi et al. | 378/98.12 |
| 6,411,848 | B2 | 6/2002 | Kramer et al. | 607/9 |
| 6,421,412 | B1 | 7/2002 | Hsieh et al. | 378/9 |
| 6,456,867 | B2 | 9/2002 | Reisfeld | 600/407 |
| 6,468,265 | B1 | 10/2002 | Evans et al. | 606/1 |
| 6,490,475 | B1 | 12/2002 | Seeley et al. | 600/426 |
| 6,490,479 | B2 | 12/2002 | Bock | 600/518 |
| 6,504,894 | B2 | 1/2003 | Pan | 378/8 |
| 6,549,606 | B1 | 4/2003 | Vaillant et al. | 378/4 |
| 6,556,695 | B1 | 4/2003 | Packer et al. | 382/128 |
| 6,584,343 | B1 | 6/2003 | Ransbury et al. | 600/509 |
| 6,650,927 | B1 | 11/2003 | Keidar | 600/424 |
| 6,950,689 | B1 | 9/2005 | Willis et al. | |
| 7,047,060 | B1 | 5/2006 | Wu | |
| 2002/0010392 | A1 | 1/2002 | Desai | 600/374 |
| 2002/0042570 | A1 | 4/2002 | Schaldach et al. | |
| 2002/0046756 | A1 | 4/2002 | Laizzo et al. | 128/899 |
| 2002/0138105 | A1 | 9/2002 | Kralik | 607/9 |
| 2003/0018251 | A1 | 1/2003 | Solomon | 600/427 |
| 2003/0023266 | A1 | 1/2003 | Borillo et al. | 606/200 |
| 2003/0028182 | A1 | 2/2003 | Sanchez et al. | 606/34 |
| 2003/0097219 | A1 | 5/2003 | O'Donnell et al. | 702/19 |
| 2003/0120264 | A1 * | 6/2003 | Lattouf | 606/1 |
| 2003/0187358 | A1 | 10/2003 | Okerlund et al. | 600/443 |
| 2003/0220557 | A1 | 11/2003 | Cleary et al. | 600/409 |
| 2004/0027347 | A1 | 2/2004 | Farsaie | 345/419 |
| 2004/0087850 | A1 | 5/2004 | Okerlund et al. | 600/407 |
| 2004/0225212 | A1 | 11/2004 | Okerlund et al. | 600/407 |
| 2004/0225328 | A1 | 11/2004 | Okerlund et al. | 607/9 |
| 2004/0225331 | A1 | 11/2004 | Okerlund et al. | 607/14 |

FOREIGN PATENT DOCUMENTS

| | | |
|---|---|---|
| EP | 1321101 A2 | 12/2002 |
| WO | WO 91/07726 | 5/1991 |
| WO | WO 96/10949 | 4/1996 |

OTHER PUBLICATIONS

Wahle et al. 3D Heart Vessel Reconstruction from Biplane Angiograms. IEEE Computer Graphics and Applications. 16(1): pp. 65-73. Jan. 1996.*

Derumeaux et al. Doppler Tissue Imaging Quantitates Regional Wall Motion During Myocardial Ischemia and Reperfusion. Circulation. 97: pp. 1970-1977. 1998.*

Mair et al. Epicardial Lead Implantation Techniques for Biventricular Pacing via Left Lateral Mini-Thoracotomy, Video-Assisted Thoracoscopy, and Robotic Approach. The Heart Surgery Forum. 6(5): pp. 412-417. Mar. 2003.*

Toshiko Nakai, Michael D. Lesh, Edward P. Gerstenfeld, Renu Virmani, Russell Jones and Randall J. Lee; "Percutaneous Left Atrial Appendage Occlusion (PLAATO) for Preventing Cardioembolism: First Experience in Canine Model", Circulation 2002; 105;2217-2222; originally published online Apr. 15, 2002; American Heart Association; http://circ.ahajounals.org/cgi/content/full/105/18/2217.

PCT Search Report for PCT/US2004/020909.

F. H.M. Wittkampf et al.; "Loca Lisa—New Technique for Real-Time 3-Dimensional Localization of Regular Intracardiac Electrodes;" Circulationh; 1999; 99: 1312-1317.

"CardilQ" product description, [online], http://egems.gehealtcare.com/geCommunity/Europe/flex_trial/awFlexTrial/aw3_1/eflextrial [retrieved 12/01/2004].

H. Nikagawa et al., "Role of the Tricuspid Annulus and the Eustachian Valve/Ridge on Atrial Flutter: Relevance to Catheter Ablation of the Septal Isthmus and a New Technique for Rapid Identification of Ablation Success;" Circulation 1996; 94:407-24.

L. Gepstein et al., "A Novel Method for Nonfluoroscopic Catheter-Based Electroanatomical Mapping of the Heart: In Vitro and In Vivo Accuracy Results;" Circulation 1997; 95:1611-22.

S. Shpun et al., "Guidance of Radiofrequency Endocardial Ablation with Real-time Three-dimensional Magnetic Navigation System;" Circulation 1997; 96:2016-21.

J. Sra et al., "Electroanatomic Mapping to Identify Breakthrough Sites in Recurrent Typical Human Flutter;" Paceing Clin. Electrophysiol 2000; 23:1479-92.

R.J. Schilling et al.; "Simultaneous Endocardial Mapping in the Human Left Ventricle Using a Noncontact Catheter: Comparison of Contact and Reconstructed Electrograms During Sinus Rhythm;" Circulation 1998; 98:997-98.

C. C. Gornick et al., "Validation of a New Noncontact Catheter System for Electroanatomic Mapping of Left Ventricular Endocardium;" Circulation 1999; 99:829-835.

J. Sra et al., "Noncontact Mapping for Radiofrequency Ablation of Complex Cardiac Arrhythmias;" J. Interven. Cardiac Electrophysiol 2001; 5:323-331.

N. M.S. de Groot et al., "Three-Dimensional Catheter Positioning During Radiofrequency Ablation in Patients: First Application of a Real-Time Position Management System;" J. Interven. Cardiac Electrophysiol 2001; Nov. 11(11):1183-92.

J. Schreieck et al., "Radiofrequency Ablation of Cardiac Arrhythmias Using a Three-Dimensional Real-Time Position Management and Mapping System;" Pacing Clin. Ekectrophysiol, Dec. 2002, 25(12):1699-707.

F. Wittkampf et al., "Real-Time, Three-Dimensional, Nonfluoroscopic Localization of the Lasso Catheter;" J. Interven. Cardiac Electrophysioll 2002, 13:630.

J. Sra et al., "Cardiac Chamber Geometry Construction, Catheter Navication and Ablation Using Cutaneous Patches;" Supplement to Circulation Oct. 2003, 108 (17): IV-585, Abstract 2667.

J. Sra et al., "Three-Dimensional Right Atrial Geometry Construction and Catheter Tracking Using Cutaneous Patches;" J. Interven. Cardiac Electrophysiol, 2003 14:897.

Z. Zhang; "Iterative Point Matching for Registration of Free-Form Curves;" Inria 1992, pp. 1-40.

C.L. Grines et al.; "Functional Abnormalities in Isolated Left Bundle Branch Block: The Effect of Interventricular Asynchrony;" Circulation; 1989; 79:845-53.

H. B. Xia et al., "Differing effects of right ventricular pacing and left bundle branch block on left ventricular function;" Br. Heart J., 1993; 69:166-173.

S. Cazeau et al., "Effects of Multisite Biventricular Pacing in Patients with Heart Failure and Intraventricular Conduction Delay;" N. Engl. J. Med. 2001; 344:873-880.

M. V. Pitzalis et al., "Cardiac Resynchronization Therapy Tailored by Echocardiographic Evaluation of Ventricular Acnchrony;" J. Am. Coll. Cardiol. 2002; 40:1615-22.

W. T. Abraham et al., "Cardiac Resynchronization in Chronic Heart Failure;" N. Engl. J. Med. 2002; 346:1845-1853.

C. A. Pelizzari et al., "Accurate Three-Dimensional Registration of CT, PET, and/or MR Images of the Brain;" *J. Comput. Assist. Tomogr.* 1989; 13:20-26.

A.C. Evans et al.; "MRI-PET Correlation in Three Dimensions Using a Volume-of-Interest (VOI) Atlas;" *J. Cerb Flow Metab.* 1991; 11:A69-A78.

R.P. Woods et al.; "Rapid Automated Algorithm for Aligning and Reslicing PET Images;" *Journal of Computer Assisted Tomography*, 1992; 16:620-633.

B.A. Ardekani et al.; "A Fully Automatic Multimodality Image Registration Algorithm;" *Journal of Computer Assisted Tomography*; 1995; 19:615-623.

L. Thurfell et al.; "Registration of Neuroimaging Data: Implementation and Clinical Applications;" *American Society of Neuroimaging*; 2000; 10:39-46.

S. A. Ben-Haim et al.; "Nonfluoroscopic, in vivo navigation and mapping technology;" *Nature Medicine*; 1996, 2:1393-5.

B. Taccardi et al.; "A new intracaitary probe for detecting the site of origin of ectopic ventricular beats during one cardiac cycle;" *Circulation*; 1987; 75:272-81.

F. H.M. Wittkampf et al.; "New Technique for Real-Time 3-Dimensional Localization of Regular Intracardiac Electrodes;" *Circulation*; 1999; 99:1312-17.

V. Fuster et al. "ACC/AHA/NASPE 2002 Guidelines Update for Implantation of Pacemakers and Antiarrhythmia Devices;" J. Am. Coll. Cardiol 2001; 38:1-47.

D. R. Ney "Volumetric Rendering of Computed Tomography Data: Principles and Techniques;" *IEEE Computer Graphics and Applications*; 1990; 24-32.

N.M. Alpert et al., "The Principal Axes Transformation—A Method for Image Registration;" *The Journal of Nuclear Medicine*; 1990; 31:1717-1722.

P.A. van den Elsen et al.; "Medical Image Matching—A Review with Classification;" *IEEE Engineering in Medicine and Biology*, 1993; 26-38.

G. T. Barnes et al.; "Conventional and Spiral Computed Tomography: Physical Principles and Image Quaility Considerations;" *Computed Body Tomography*, 1998, Lippincot-Raven, Philadelphia, PA pp. 1-20.

Milan Sonka and J. Michael Fitzpatrick (eds); *Handbook of Medical Imaging vol. 2. Medical Image Processing and Analysis*; pp. 129-174 & 447-506.

W. M. Feinberg et al.; "Prevalence, Age Distribution, and Gender of Patients with Atrial Fibrillation;" *Arch. Intern. Med. vol. 155*; Mar. 1995; pp. 469-473.

C. Pappone, S. Rosanio, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

ACC/AHA/ESC Practise Guidelines; Eur. Heart J., vol. 22, issue 20, Oct. 2001; pp. 1854-1923.

J. L. Cox, J. P. Boineau, R. B. Schuessler, T. B. Ferguson, Jr., M. E. Cain, B. D. Lindsay, P. B. Corr, K. M. Kater, D. G. Lappas; "Operations for Atrial Fibrillation;" Electrophysiology, Pacing and Arrhythmia, Clin. Cardiol. 14, 1991; pp. 827-834.

W. M. feinberg, J. L. Blackshear, A. Laupacis, R. Kronmal, and R. G. Hart; "Prevalence, Age Distribution, and Gender of Patients with Atrial Fibrillation;" Arch Intern Med., vol. 155, Mar. 13, 1995; pp. 469-473.

M. Haissaguerre, P. Jais, S. C. Shah, A. Takahashi, M. Hocini, G. Quiniou, S. Garrigue, A. Le Mouroux, P. Le Metayer, and J. Clementy; "Spontaneous Initiation of Atrial Fibrilliation by Ectopic Beats Originating in the Pulmonary Viens;" The New England Journal of Medicine, vol. 339, No. 10, Sep. 3, 1998; pp. 659-668.

"Current Problems in Cardiology- Atrial Fibrilliation: Epidemiology, Mechanisms, and Management;" Current Problems in Cardiology, Jul. 2000; pp. 406-524.

M. D. Leash, T. Trepelse, H. Omran, A. Bartorelli, P. Della Bella, T. Nakai, M. Reisman, D. fleschenberb, U. Krumsdorf, and D. Scherer; "Tiny Device Blocks 'Usless' Part of Heart, prevents blood clots;" Journal Report; American Heart Association; Apr. 9, 2002.

Ellen Barlow; "Operating in 3-D" found at www.med.harvard.edu/publications/HMAB/196fo3d.html.

Genevieve Derumeaux et al., Doppler Tissue Imaging Quantitates Regional Wall Motion During Myocardial Ischemia and Reperfusion, Circulation Journal of the American Heart Association, Circulation 1998; 97; 1970-1977.

Olivier Gerard et al., Efficient Model-Based Quantification of Left Ventricular Function in 3-D Echocardiography. IEEE Transactions on Medical Imaging, 21 (9): pp. 1059-1068, Sep. 2002.

Wahle et al., 3D Heart Vessel Reconstruction from Biplane Angiograms, IEEE Computer Graphics and Applications, 16(1): pp. 65-73, Jan. 1996.

Helmut Mair et al., Epicardial Lead Implantation Techniques for Biventricular Pacing via Left Lateral Mini-Thoracotomy, Video Assisted Thoracoscopy and Robotic Approach, The Heart Surgery Forum, 6(5): pp. 412-417, Mar. 2003.

Sra et al., "Registration of Three-Dimensional Left Atrial Computed Tomographic Images With Projection Images Obtained Using Fluoroscopy", Circulation 2005; 112: 3763-3768.

Ellen Barlow; "Operating in 3-D" found at www.med.harvard.edu/publications/HMAB/196fo3d.html, date unknown.

\* cited by examiner

Pre-systole        End-systole

CARDIAC IMAGING SYSTEM AND METHOD FOR QUANTIFICATION OF DESYNCHRONY OF VENTRICLES FOR BIVENTRICULAR PACING

BACKGROUND OF THE INVENTION

The present disclosure relates generally to cardiac rhythm management systems and, more particularly, to a cardiac imaging system and method for quantification of desynchrony of ventricles for biventricular pacing.

It is estimated that approximately 6-7 million people in the United States and Europe alone have congestive heart failure (CHF), with ischemic and idiopathic cardiomyopathies being the most common causes of CHF. In about 20-50% of patients having CHF, the associated electrocardiograms are characterized by prolonged PR intervals and wide QRS complexes. Moreover, about 29% of these patients have left bundle branch block (LBBB).

In a normal heartbeat, the electrical conduction begins in the sinoatrial (SA) node (a small group of muscle cells in the upper right part of the upper right heart chamber, i.e., the right atrium). Impulses sent out by the SA node spread quickly throughout the upper heart chamber and across the atrioventricular (AV) node. Once past the AV node, the electrical signals travel through a bunch of fibers called the bundle of His, which passes the signals the rest of the way through the wall separating the upper and lower heart chambers, splitting down the right and left bundle branches to reach each part of the ventricles.

However, in those patients with CHF and LBBB, a long mechanical delay in the left side of the heart leads to a delayed left ventricular ejection due to delayed left ventricular depolarization. In other words, LBBB causes an asymmetrical contraction of the right and left ventricles. In addition, this condition (also known as desynchrony) may also result in different regions of the left ventricle not contracting in a coordinated fashion. This irregular motion is characterized by shortening of the septum, followed by stretching of the lateral wall. Subsequently, the lateral wall then shortens and the septum stretches, thereby causing an ineffective contraction of the left ventricle.

Cardiac resynchronization therapy, also known as biventricular pacing, is an interventional procedure in which both the right ventricle and left ventricle of the heart are paced simultaneously to improve heart pumping efficiency. In one example of a conventional biventricular pacing procedure, both the right ventricle and right atrial leads are first positioned. Then, a sheath is positioned within the coronary sinus (CS) and a CS angiogram is performed in order to delineate a suitable branch for left ventricle lead placement. After a suitable branch is identified, the left ventricle lead is placed in the posterior or posterolateral branch of the CS. Once positioned, the right and left ventricle leads are paced simultaneously, thus achieving synchronization with atrial contraction.

For many patients, cannulating the CS is the one-step procedure of choice for biventricular lead placement. However, in over 20% of these patients, lead placement in the CS may be unsuccessful or a very lengthy procedure, or the lead may become dislodged from the CS. Other difficulties with this lead placement procedure may also include unavailability of a suitable CS branch, significant rotation of the CS due to left atrium and left ventricle dilation, and the presence of the Thesbesian valve therein. In most instances, these problems are identified only at the time of the interventional procedure, and thus the procedure is typically either completely abandoned or the patient is brought back into the operating room for a second procedure where, through a surgical incision (an expensive and invasive procedure) the left ventricle lead is placed epicardially.

Unfortunately, epicardial lead placement is not without its own pitfalls, some of which include: a limited view of the posterolateral area of the left ventricle using minithoracotomy; the limitation of placement sites providing reasonable pacing and sensing parameters; the inability to determine the distance of the left ventricle from the thoracic wall; the inability to identify the posterolateral or other areas of the left ventricle that contracts last; the potential risk of damaging the coronary arteries and veins; the increased level of difficulty due to the presence of extrapericardial fat; the lack of visualization of normal versus scarred tissue; and the difficulty in identifying the ideal pacing position as a result of one or more of the above.

Accordingly, there is a need for an improved system and method for quantifying the desynchrony of the right and left ventricles so as to provide information for planning biventricular pacing interventional procedures.

BRIEF DESCRIPTION OF THE INVENTION

The above discussed and other drawbacks and deficiencies of the prior art are overcome or alleviated by a method for quantifying cardiac desynchrony of the right and left ventricles. In an exemplary embodiment, the method includes obtaining cardiac acquisition data from a medical imaging system, and determining a movement profile from the cardiac acquisition data. The movement profile is directed toward identifying at least one of a time-based contraction parameter for a region of the left ventricle (LV), and a displacement-based contraction parameter for a region of the LV. The determined movement profile is visually displayed by generating a 3D model therefrom.

In another aspect, a method for planning biventricular pacing lead placement for a patient includes obtaining cardiac acquisition data from a medical imaging system, and determining a movement profile from the cardiac acquisition data. The movement profile is directed toward identifying at least one of a time-based contraction parameter for a region of the left ventricle (LV), and a displacement-based contraction parameter for a region of the LV. The determined movement profile is visually displayed by generating a 3D model therefrom, and one or more coronary vessels are visualized on the generated 3D model. At least one suitable region is identified on the left ventricle wall for epicardial lead placement.

In still another aspect, a method for planning biventricular pacing lead placement for a patient includes obtaining cardiac acquisition data from a medical imaging system, and determining a movement profile from the cardiac acquisition data. The movement profile is directed toward identifying at least one of a time-based contraction parameter for a region of the left ventricle (LV), and a displacement-based contraction parameter for a region of the LV. The determined movement profile is visually displayed by generating a 3D model therefrom, and one or more coronary vessels are visualized on the generated 3D model. At least one suitable region is identified on the left ventricle wall for epicardial lead placement. In addition, coronary sinus branches closest to the at least one suitable region are identified and displayed or more left ventricle anatomical landmarks are identified on the 3D model, and saved views of the 3D model are registered on an interventional system for visualization and identification of a minimally invasive route for epicardial lead placement.

In still another aspect, a system for quantifying cardiac desynchrony of the right and left ventricles includes a medical imaging system for obtaining cardiac acquisition data. An image generation subsystem is configured to receive the acquisition data and for determining a movement profile from the cardiac acquisition data. The movement profile is directed toward identifying at least one of a time-based contraction parameter for a region of the left ventricle (LV), and a displacement-based contraction parameter for a region of the LV. An operator console is configured for visually displaying the determined movement profile by generating a 3D model therefrom.

In still another aspect, a system for planning biventricular pacing lead placement for a patient includes a medical imaging system for generating acquisition data. An image generation subsystem is configured for receiving the acquisition data and for determining a movement profile from the cardiac acquisition data. The movement profile is directed toward identifying at least one of a time-based contraction parameter for a region of the left ventricle (LV), and a displacement-based contraction parameter for a region of the LV. An operator console is configured for visually displaying the determined movement profile by generating a 3D model therefrom, the operator console further configured for visualizing one or more coronary vessels on said generated 3D model. A workstation includes post-processing software for registering saved views of the 3D model on an interventional system. The interventional system is configured for visualizing one or more of the registered saved views therewith and for identifying a minimally invasive route for epicardial lead placement.

BRIEF DESCRIPTION OF THE DRAWINGS

Referring to the exemplary drawings wherein like elements are numbered alike in the several Figures.

DETAILED DESCRIPTION OF THE INVENTION

Disclosed herein is a cardiac imaging system and method for quantifying the desynchrony of the right and left ventricles so as to provide information for planning biventricular pacing interventional procedures enabling the practitioner (e.g., electrophysiologist, cardiologist, surgeon) to plan in advance the approach to take for the procedure. LV contractility can be visualized to identify the best location for placement of the LV epicardial pacing lead by, for example, determining the LV region that is the "last to contract" (i.e., a time-based contraction parameter). As used hereinafter, the term "last to contract" may be quantified as either last to start contraction or last to complete contraction by the exemplary method described in greater detail below. Alternatively, LV contractility can be visualized by determining the LV region that exhibits the most/least amount of displacement with respect to a starting position at a given point in the cardiac cycle (i.e., a displacement-based contraction parameter).

Figure 3:
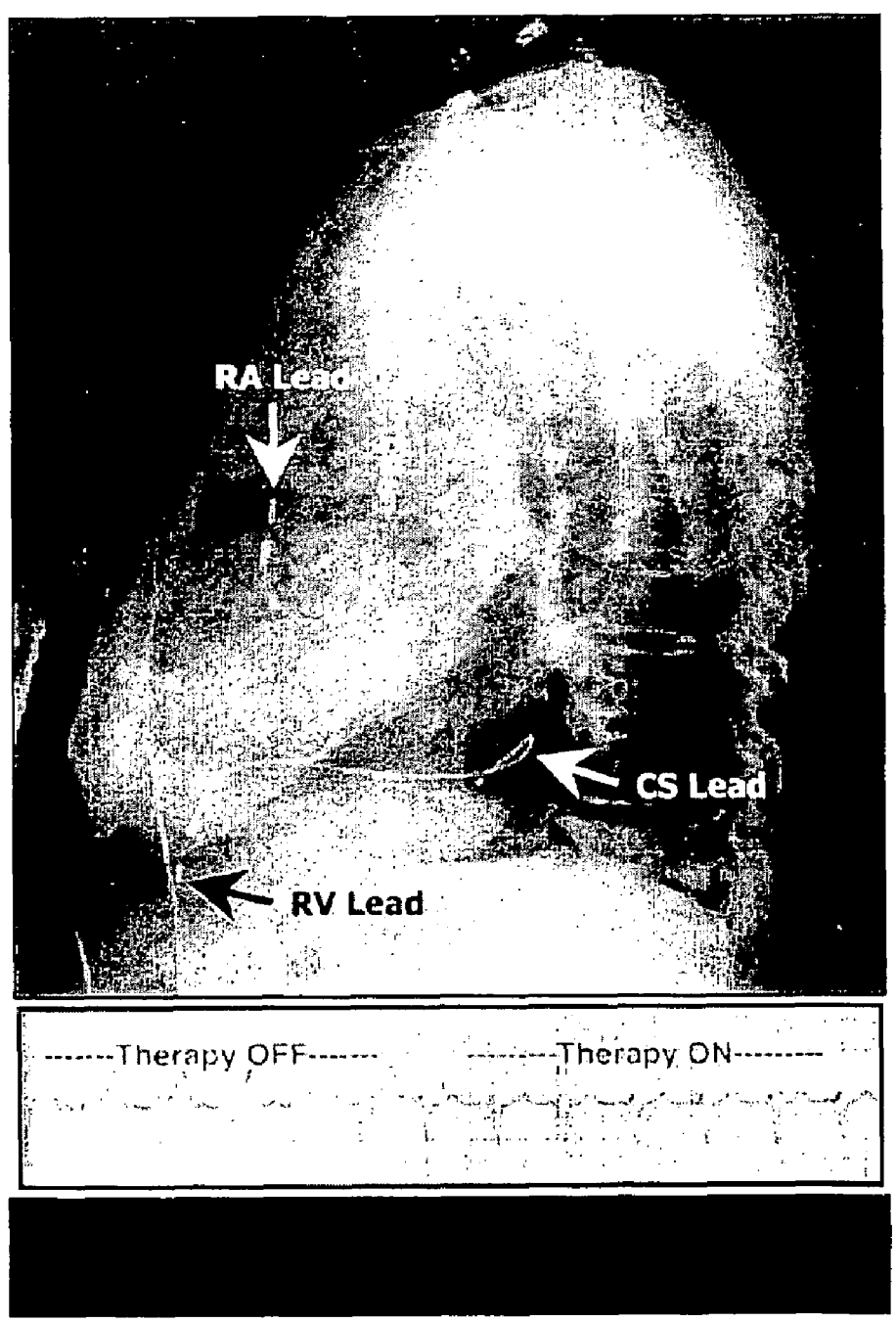
FIG. 3 is a fluoroscopic image illustrating a typical procedure for bi-ventricular pacing.

As stated previously, cardiac resynchronization therapy (where both the right ventricle (RV) and the left ventricle (LV) are paced simultaneously) has been shown to be effective in improving cardiac function in patients with CHF and LBBB. FIG. 3 is a fluoroscopic image illustrating a typical procedure for bi-ventricular pacing that includes positioning the pacing electrodes in the right atrium and RV, and placing another pacing electrode on the LV via coronary sinus or epicardially in an open chest procedure.

However, irrespective of the particular method employed to place the LV pacing electrode, it is important to determine the region of the LV that is contracting last or that displaces the most/least. This region is the optimal location of the pacing lead as it provides the most benefit to the patient. Accordingly, the present disclosure describes a method to quantify the mechanical delays of different segments of the LV, and to identify the region that contracts last and/or identify the region which displaces the most. Furthermore, this approach may similarly be used to determine the contraction in the RV as well. Although the exemplary embodiments illustrated hereinafter are described in the context of a computed tomography (CT) imaging system, it will be appreciated that other imaging systems known in the art (e.g., magnetic resonance, ultrasound, 3D fluoroscopy) are also contemplated with regard to planning biventricular epicardial lead placement.

In addition, with a more detailed three-dimensional (3D) geometrical representation of the LV and its relationship to the thoracic wall, the practitioner can identify the contraction delays of the LV wall, the presence of fat, the location and orientation of the major blood vessels and their branches and viable tissue which can be used for placement of the LV lead. Thus, the information obtained from the cardiac imaging system eliminates the need to place the lead blindly, avoiding many of the problems involved in using this approach, and allows for direct epicardial lead placement via a surgical incision or endoscopic approach at the most beneficial location. The location of the incision and the lead placement can be planned in advance. Moreover, the epicardial lead may be registered with an interventional system or fluoroscopy to enable precise placement of the lead.

Figure 1:
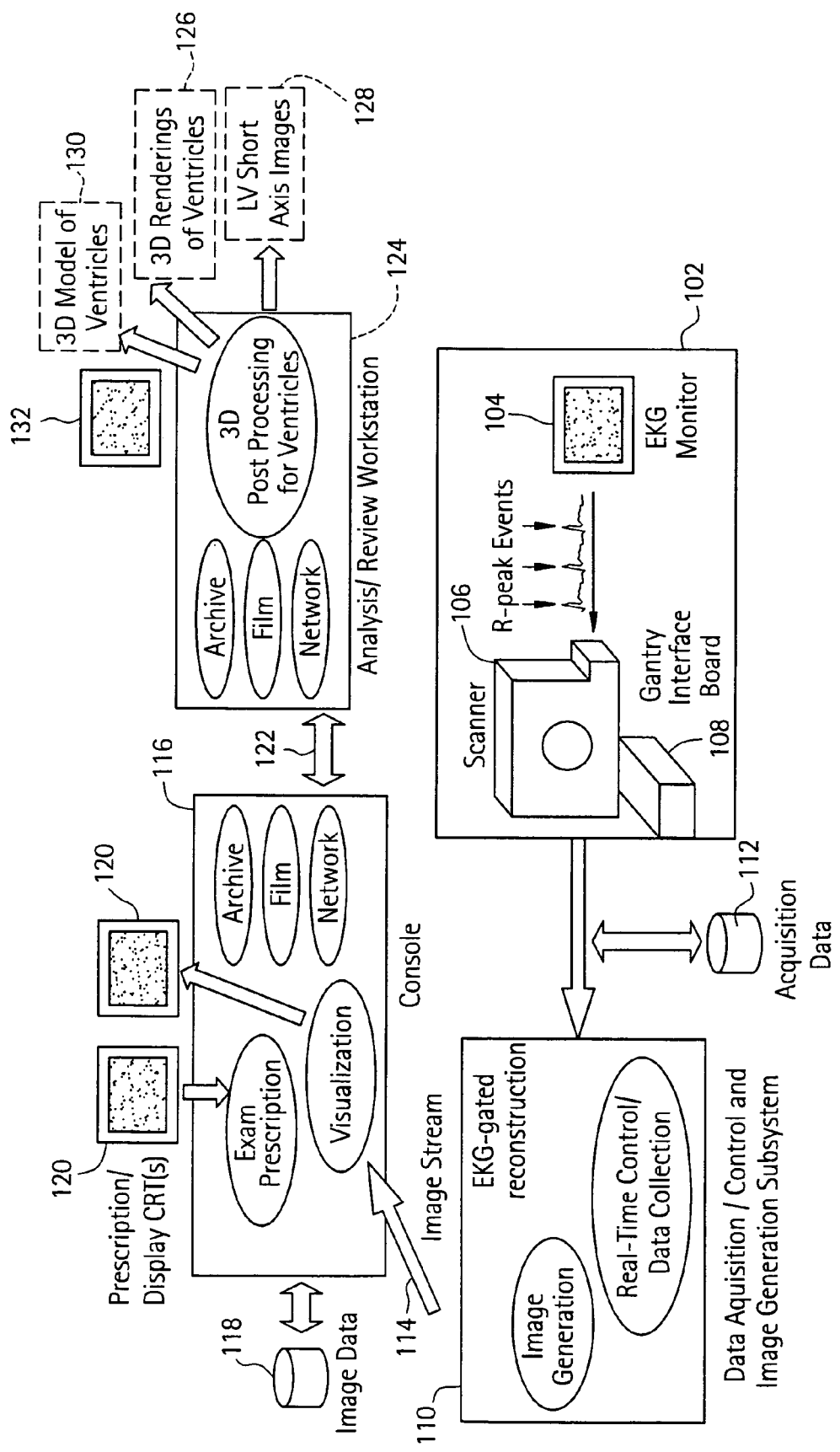
FIG. 1 is a schematic diagram of a medical imaging system, such as a computed tomography (CT) system, suitable for planning biventricular lead pacing, in accordance with an embodiment of the invention.

Referring now to FIG. 1, there is shown an overview of an exemplary cardiac computed tomography (CT) system 100 with support for cardiac imaging. Again, it should be understood that the cardiac CT system 100 is presented by way of example only, since other imaging systems known in the the art (e.g., magnetic resonance, ultrasound, 3D fluoroscopy) may also be used in an embodiment of the present invention. A scanner portion 102 of the system 100 includes an EKG monitor 104 that outputs R-peak events into a scanner 106 through a scanner interface board 108. A suitable example of scanner interface board 108 is a Gantry interface board, and can be used to couple an EKG system to the scanner. The cardiac CT subsystem defined by scanner portion 102 utilizes EKG-gated acquisition or image reconstruction capabilities to image the heart free of motion in its diastolic phase, as well as in multiple phases of systole and early diastole.

Data are outputted from the scanner portion 102 into a subsystem 110 that includes software for performing data acquisition, data control and image generation. In addition, data that is outputted from the scanner 106, including R-peak time stamps, is stored in an acquisition database 112. Acquisition is performed according to one or more acquisition protocols that are optimized for imaging the heart and specifically the LV diastole and multiple phases in systole and early diastole. Image generation is performed using one or more optimized 3D protocols for automated image segmentation of the CT image dataset for the LV and thoracic wall.

The image data stream 114 is sent to an operator console 116. The data used by software at the operator console 116 for exam prescription and visualization is stored in an image database 118, along with the data from the image data stream 114. Display screens 120 are provided to the operator of the exam prescription and visualization processes. The image data may be archived, put on film or sent over a network 122 to a workstation 124 for analysis and review, including 3D post processing. The post processing software depicted in the workstation 124 includes one or more optimized 3D protocols and short axis protocols from an automated image segmentation of the CT image dataset for the LV anatomy, movement of LV walls during systole (i.e., LV contractility), epicardial fat location, location of viable tissue, blood vessels and their branches and orientation.

The 3D protocols and short axis protocols of the post processing software enable the software to provide views of the LV, including blood vessels, branches and slow motion cine of the LV, particularly the posterolateral wall or other areas of the LV. These special views and video (cine) clips may be saved into a 3D rendering of ventricle files 126 and LV short axis images 128 for use by the practitioner for interventional planning and procedure. The post processing software also provides for the export of detailed 3D models 130 of the thoracic wall and ventricle surfaces. The 3D models 130 (which may be implemented through color coding, contouring, movie views, etc.) may be viewed on display screen 132 associated with workstation 124 and are configured to include geometric markers inserted into the volume at landmarks of interest such that the thoracic wall and the LV are visualized in a translucent fashion with the opaque geometric landmarks.

In addition, the 3D models 130 may be in exported in any of several formats, including but not limited to: a wire mesh geometric model, a set of contours, a segmented volume of binary images, and a DICOM (Digital Imaging and Communications in Medicine) object using the radiation therapy (RT) DICOM object standard or similar object. Other formats known in the art can also be used to store and export the 3D models 130.

Figure 2:
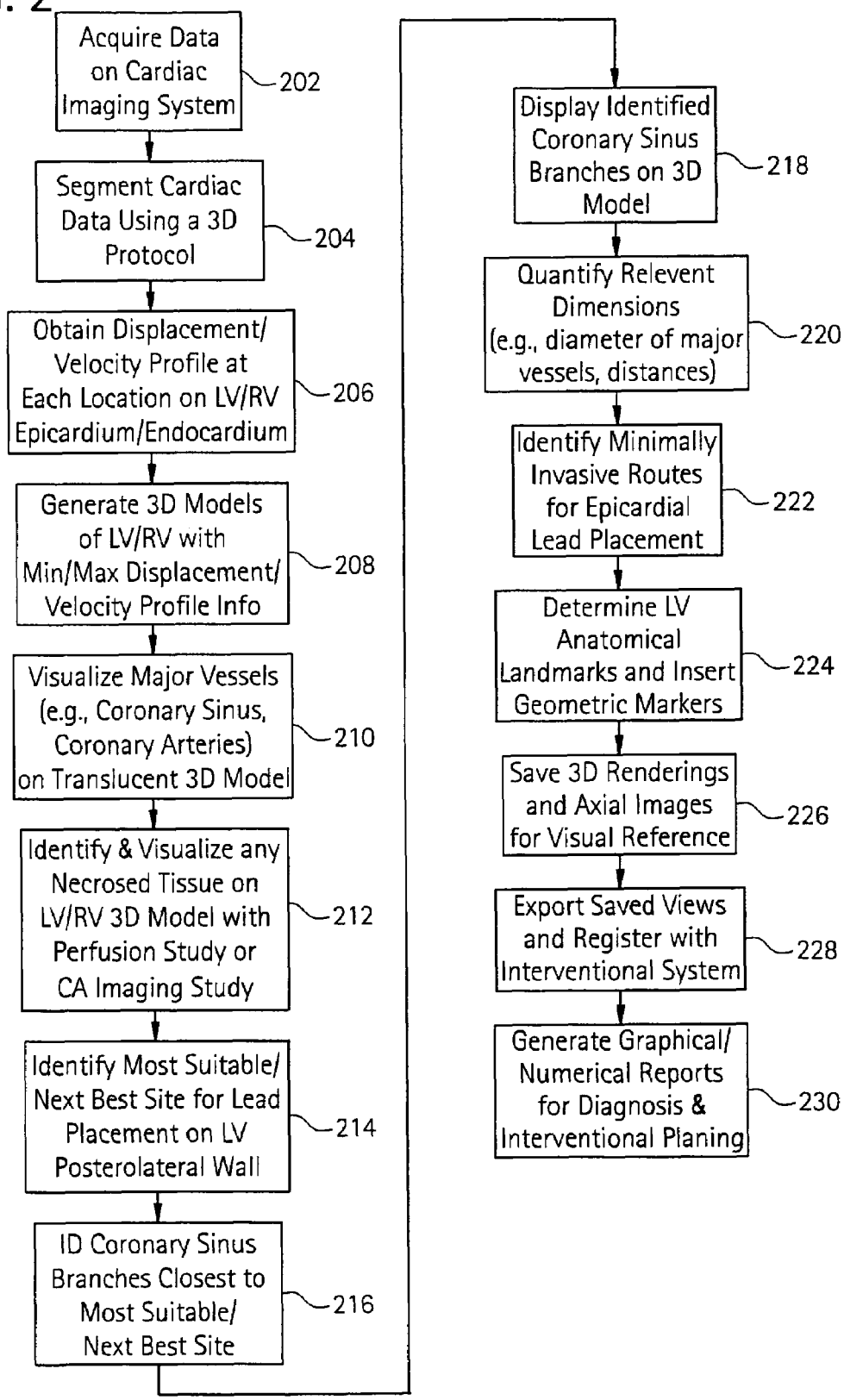
FIG. 2 is a flow diagram of a method for planning biventricular pacing epicardial lead placement, in accordance with a further embodiment of the invention.
Figure 4:
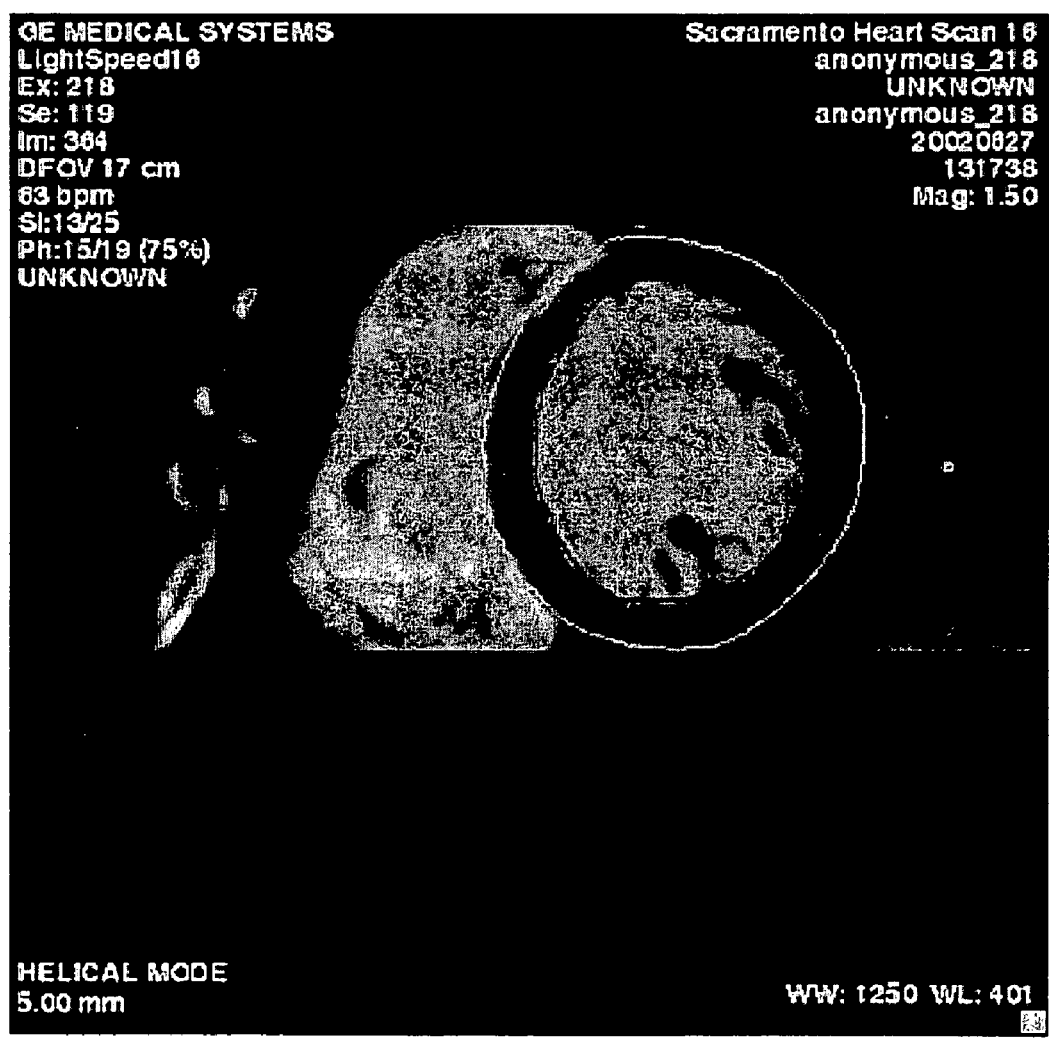
FIG. 4 illustrates an image obtained through automatic detection of the endocardium and epicardium of the left ventricle.

Referring now to FIG. 2, there is shown a flow diagram 200 illustrating a method for interventional planning of bi-ventricular pacing lead placement, in accordance with a further embodiment of the invention. Beginning at block 202, a volume of data is initially acquired on the cardiac CT system, using a protocol that is preferably optimized for the thoracic wall, RV and LV regions of the heart. At block 204, the image dataset is segmented with post-processing software using a 3D protocol and short axis protocols designed to extract the surfaces of the RV, LV and the RV and LV myocardium. Automated or semi-automated procedures may be employed, where appropriate, with or without queues from the operator (e.g., location of anteroposterior, left anterior oblique, posterolateral, oblique and right anterior oblique views). FIG. 4, for example, illustrates an image obtained through automatic detection of the endocardium and epicardium of the left ventricle. This operation can be performed on short axis reformatted cardiac images for each phase and slice location to obtain the displacement profile, or on multiphase, long axis reformatted cardiac images.

Figure 5:
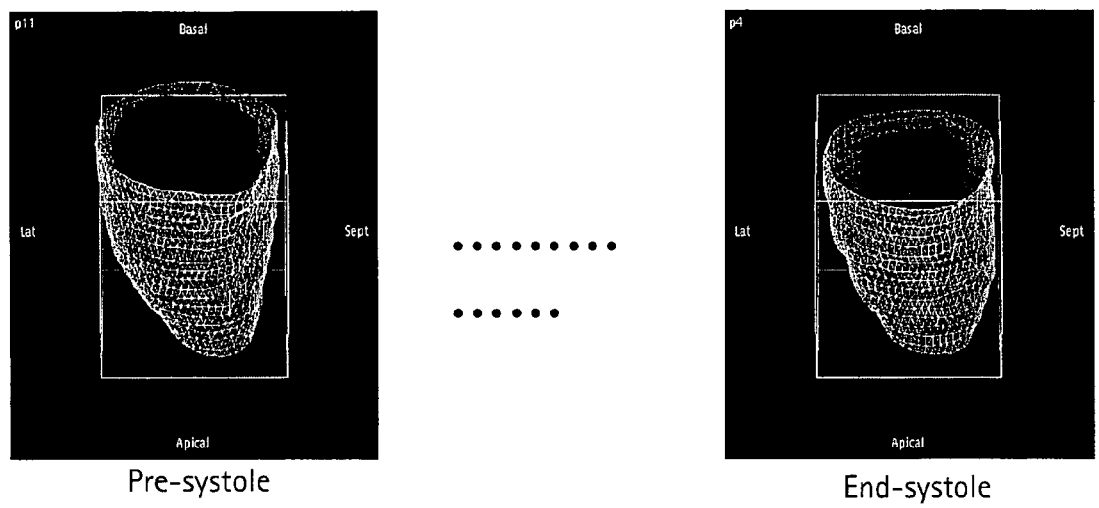
FIG. 5 is a pair of 3D cardiac CT images in wire mesh illustrating the epicardium (outer wall) and endocardium (inner wall) of the LV at pre-systole and end systole.

Referring again to FIG. 2, and as shown in block 206, a movement profile (e.g., a displacement and/or velocity profile) is then obtained at each of a designated number of locations on the LV and RV epicardium and endocardium by comparing the wall motion at each cardiac phase with respect to a reference phase. For example, this may be implemented with reference to FIG. 5, which shows a pair of 3D cardiac CT images in wire mesh illustrating the epicardium (outer wall) and endocardium (inner wall) of the LV at pre-systole and end systole. Similar images are generated for different phases therebetween in order to determine the region of posterolateral LV that contracts last. With this information, optimal epicardial lead placement location may ultimately be determined.

Figure 6:
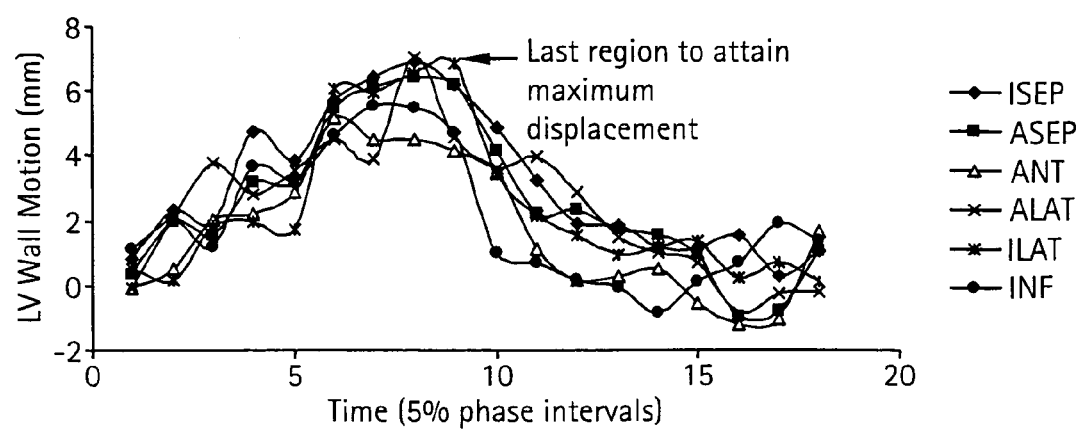
FIG. 6 is a graph illustrating an example of the LV wall displacement profile of a middle slice of the LV at six predefined regions.

FIG. 6 is a graph illustrating an example of the LV wall displacement profile of a middle slice of the LV at six predefined regions (although an additional number of regions may also be used). In an exemplary embodiment, the six regions on the LV are defined as ISEP (Inferior Septal), ASEP (Anterior Septal), ANT (Anterior), ALAT (Anterior Lateral), ILAT (Inferior Lateral) and INF (Inferior). As can be seen from the graph, the ILAT location reaches its maximum displacement (most contraction) with the greatest delay (i.e., the last region to finish contraction), and may thus be later identified as the optimal site for lead placement.

After the LV and RV movement profiles are determined (whether through minimum/maximum displacement or velocity profiles), this information is then used in the generation of a 3D model thereof, as shown in block 208 of FIG. 2. In one embodiment, generated 3D models of the LV and RV may be overlaid with a color-coded map showing the maximum (or minimum) displacement or velocity of each region. Also, the region that starts (or finishes) contraction last may be visualized by displaying the time delay of maximum velocity (or displacement) of each region on the model using additional numeric, contour line and/or color-coded displays.

Figure 7:
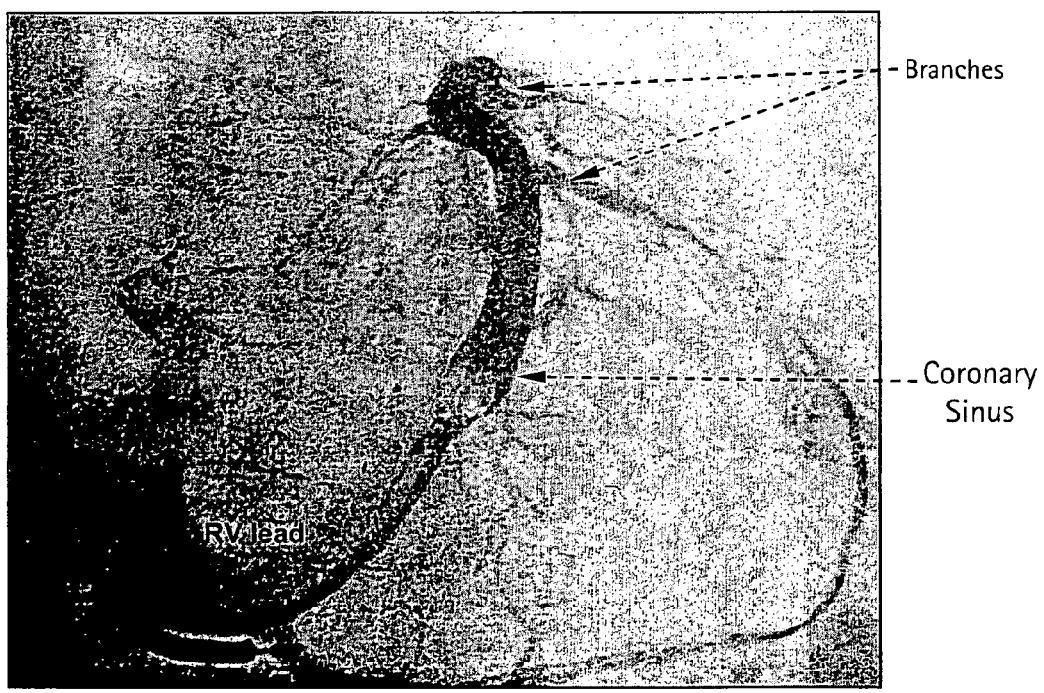
FIG. 7 is an exemplary angiogram of the coronary sinus and its branches.
Figure 8:
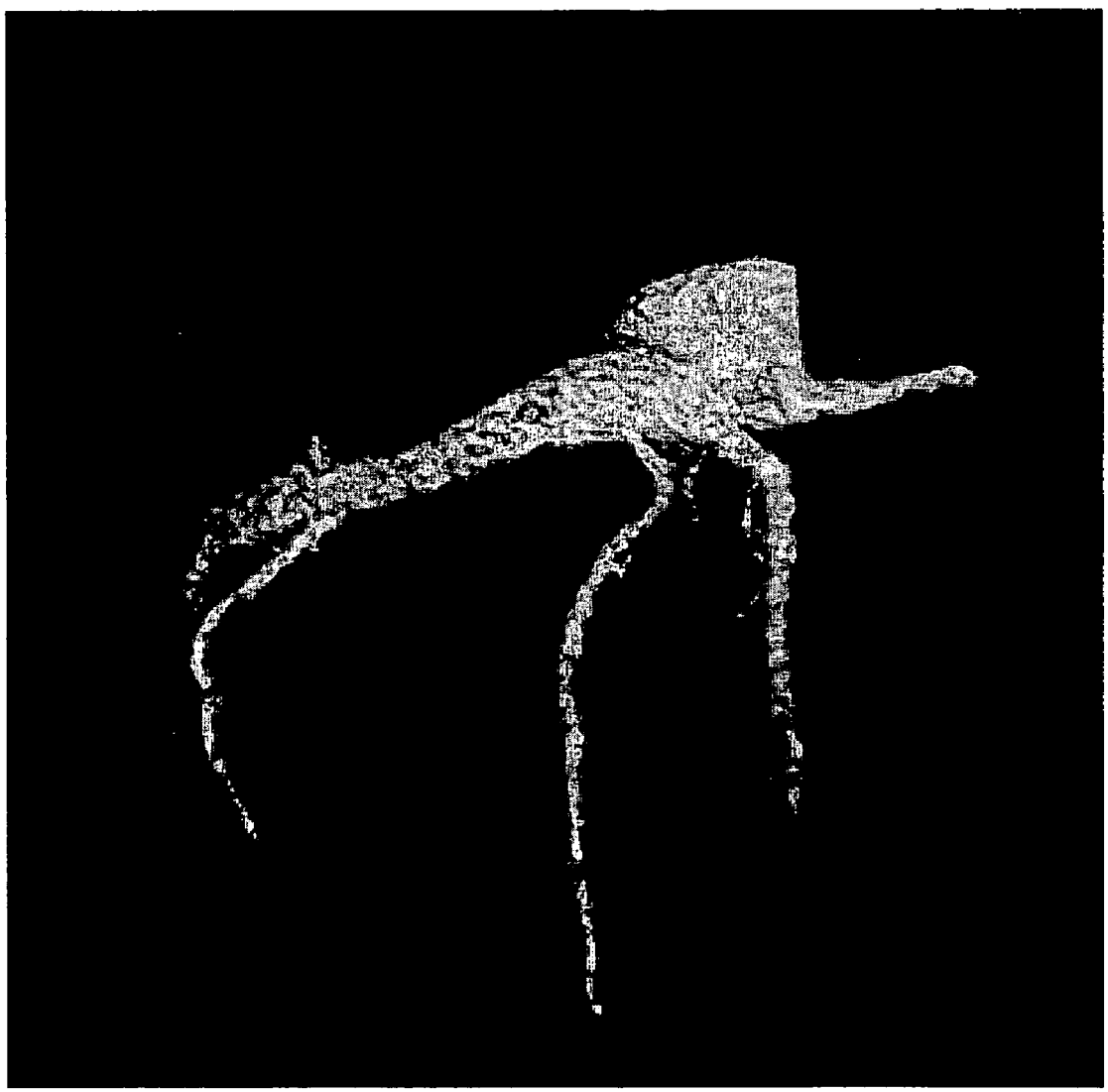
FIG. 8 is a CT segmented, 3D model of the coronary sinus and its branches.
Figure 9:
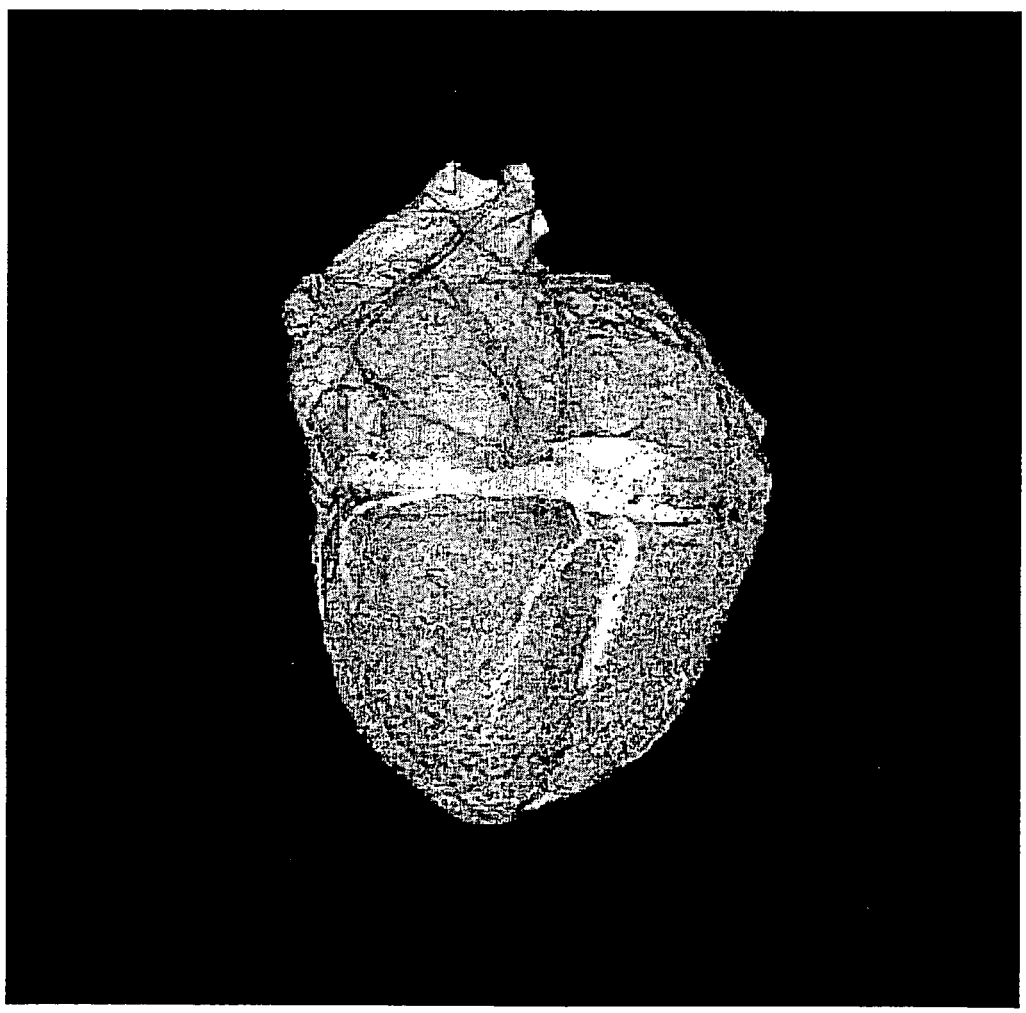
FIG. 9 is a CT segmented translucent model of heart overlaid with the coronary sinus and its branches.

Thereafter, method 200 proceeds to block 210 for visualization of the major coronary vessels and structures (e.g., the coronary sinus, coronary arteries, thoracic wall, LV walls, blood vessels and epicardial fat) on a translucent 3D model of the heart using 3D surface and/or volume rendering. Notwithstanding the location(s) of the desired epicardial pacing lead placement, the major vessel locations are also used to determine whether the lead can in fact be placed at the desired location through minimally invasive techniques. This can avoid placement of leads onto regions proximal to major vessels that may otherwise cause complications. For example, FIG. 7 is an exemplary angiogram of the coronary sinus and its branches, further illustrating the position of the RV lead with respect to the vessel locations. FIG. 8 is a CT segmented, 3D model of the coronary sinus and its branches, while FIG. 9 illustrates a CT segmented translucent model of heart overlaid with the coronary sinus and its branches.

Figure 10:
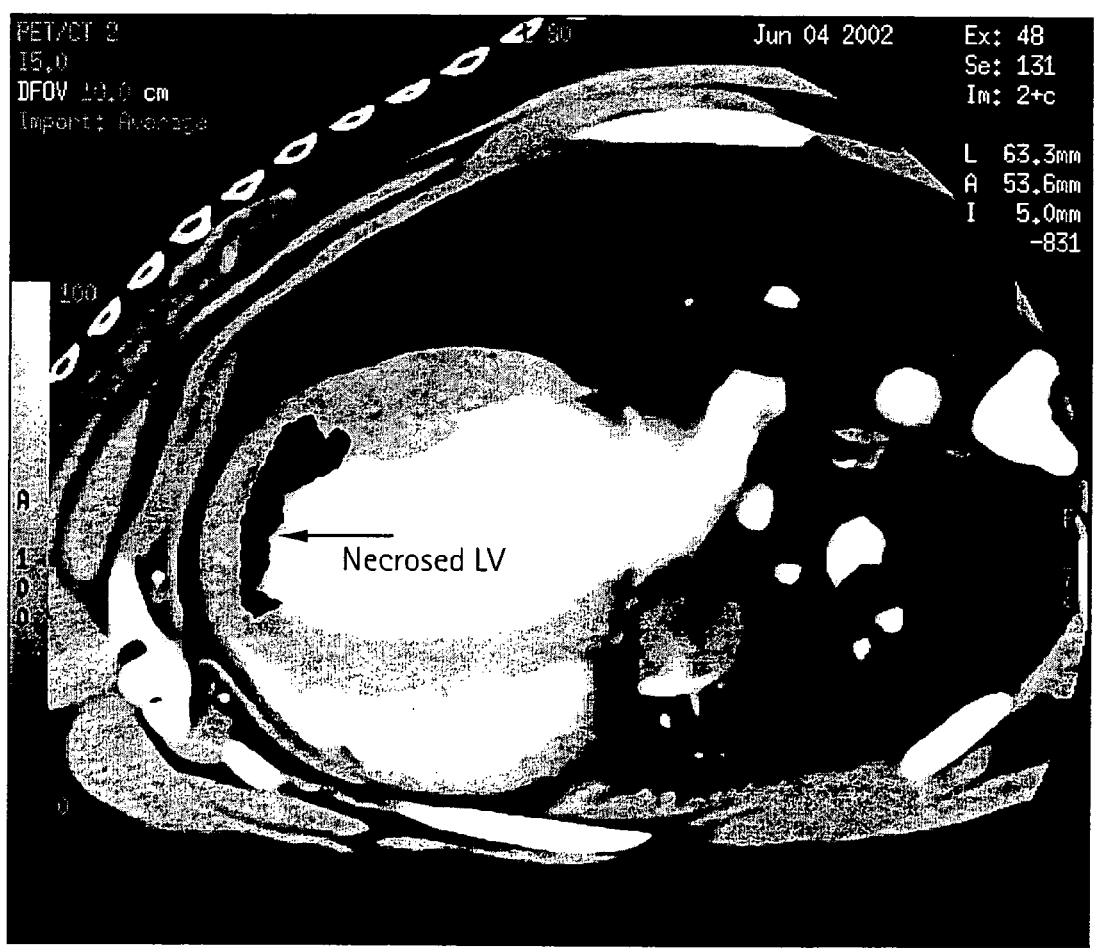
FIG. 10 is a cardiac CT image showing necrosed LV due to myocardial infarction.

As shown in block 212 of FIG. 2, method 200 further identifies and visualizes any existing necrosed tissue on the LV/RV with a perfusion study or coronary imaging study. If any such necrosed tissue is identified, then the location thereof is disqualified as the most suitable site for lead placement in order to avoid placing leads onto ineffective regions. The location of any necrotic tissue is also visualized on the 3D model of the LV and RV. An example of such a visualization is presented in FIG. 10, which illustrates a cardiac CT image showing necrosed LV due to myocardial infarction. Accordingly, given the location of the region of posterolateral LV that contracts last, the visualization of the major vessels and the location of necrosed tissue (if any), the identification of the most suitable and next most suitable site(s) for the lead placement on the LV posterolateral wall is completed, as shown in block 214 of FIG. 2.

Although the most suitable and next most suitable sites for lead placement may be identified through the above described imaging and visualization of the last to contract region, the major vessels and necrosed tissue, there is still the practical matter of being able to direct the pacing leads to those identified desired sites through minimally invasive means. Thus, method 200 proceeds to block 216, for identification of coronary sinus branches that are closest to the identified most suitable/next best suitable site. This identification may be completely automatic using image processing and pattern recognition techniques, as well as a combination of user interaction and automatic methods. As shown in block 218, any automated computation of the best route for pacing lead placement is displayed in the 3D coronary sinus model together with certain quantification data including, but not limited to, vessel diameter, degree of stenosis, length of route, and angle between the main branch and sub-branch.

The presentation of the results of the coronary sinus identification may be in the form of color-coded vessel branches on a 3D translucent heart and opaque desynchronized regions. Alternate presentations may be in the form of arrows with text or numeric codes for the CS branches overlaid on translucent heart and opaque desynchronized areas. In lieu of displaying the heart and the desynchronized areas in transparent and opaque formats, other colors and shades may be used.

Figure 11:
FIG. 11 is an image illustrating measurements of distance from the CS ostium to the posterior lateral branch.

Additionally, as shown in block 220, method 200 may further include the quantification of certain relevant dimensions, such as: the diameter/circumference of major vessels (e.g., coronary sinus, posterior vein and posterior lateral vein); the distance and angle from the coronary sinus (CS) ostium to the CS posterior branch and posterior lateral branch (as shown in FIG. 11); and the distance from the proxima of any of the above mentioned branches to the targeted lead placement location. These measurements can help in choosing the appropriate catheter size and estimating the distance that the catheter needs to be advanced in the CS before turned into the branches during a lead placement procedure.

As shown at block 222, the practitioner then identifies the most suitable area for placement of the epicardial pacing electrode on the LV wall, as well as the next best region(s) for placement thereof. In particular, the practitioner may identify the blood vessels on the epicardium of the left ventricle and eliminate the blood vessels and/or the myocardium directly under the blood vessels as a suitable region. The models also serve to provide a surgeon with a LV model and motion profile for placing an epicardial lead via an open chest procedure (i.e., a standby procedure for lead placement in the event that the coronary sinus route is not feasible).

Proceeding now to block 224, explicit geometric markers are inserted into the volume at landmarks of interest, wherein the thoracic wall and LV may be visualized in a translucent fashion with the inserted opaque geometric landmarks. As illustrated at block 226, specific 3D renderings and axial images (as DICOM images/3D models, video clips, films, multimedia formats, etc.) are saved as desired for subsequent visual reference during the interventional planning. The saved views are then exported and registered with the projection image on the fluoroscopy system or alternatively, with the tomosynthesis images of the 3D fluoroscopy system, as shown in block 228. The registration will provide an electrophysiologist with a real-time 3D visualization of the catheter with respect to the optimal lead placement.

Finally, after the interventional system is accessed and the imported, registered models therewith are visualized by the practitioner. As shown in block 230, method 200 may also be used to generate specific graphical and numerical reports (e.g., contractility profile, color-mapped 3D model, dimension measurements, etc.) to be used for diagnosis and interventional planning.

It will be appreciated that automatic techniques may be employed to perform any of the above steps by using one or more of the several computer-assisted detection, localization and visualization methods available, such as quantitative analysis of perfusion defects, localized contractility profile (LV wall movement), identification of blood vessels using the continuity of same intensity levels. Moreover, these methods could be either completely automatic when the procedure and the organ of interest is specified or partly interactive with input from the user.

It will further be appreciated that through the use of the above described method and system embodiments, the planning of bi-ventricular pacing is improved in that the imaging information generated and registered allows for an appropriately tailored approach to the interventional procedure. In choosing the appropriate approach, the duration of the procedure itself is reduced and any unnecessary procedures are also eliminated. More particularly, a detailed 3D geometric and axial representation of the quantified delays of the mechanical contractions of the LV increases the precision of the biventricular pacing procedure. The identification of necrosed myocardium, if any, enables the practitioner to avoid such areas and place the LV epicardial lead on healthy, viable myocardium.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for quantifying cardiac desynchrony of the right and left ventricles, the method comprising:

obtaining cardiac acquisition data from a medical imaging system;

determining a movement profile from said cardiac acquisition data, said movement profile directed toward identifying at least one of: a time-based contraction parameter for a region of the left ventricle (LV), and a displacement-based contraction parameter for a region of the LV;

visually displaying said determined movement profile by generating a 3D model therefrom;

based on said movement profile and said 3D model, identifying a site and a route for biventricular lead placement on the LV;

determining LV anatomical landmarks of interest and inserting geometric markers into said 3D model thereat; and registering said 3D model having said geometric markers with an interventional medical system for real-time 3D visualization of the LV and interventional lead placement thereat.

2. The method of claim 1, wherein said displacement-based contraction parameter further comprises a displacement profile for each of a plurality of designated regions.

3. The method of claim 2, wherein said displacement profile for each of a plurality of designated regions is used to identify one of said plurality of designated regions having a maximum displacement with respect to a starting position thereof at a given cardiac cycle point.

4. The method of claim 1, wherein said time-based contraction parameter further comprises last to contract information based upon displacement versus time information over a cardiac cycle, for each of a plurality of designated regions.

5. The method of claim 4, wherein a last to contract region from said plurality of designated regions is identified by determining which of said plurality of designated regions is last to attain a maximum displacement thereof.

6. The method of claim 1, wherein said time-based contraction parameter further comprises last to contract information based upon a velocity profile for each of a plurality of designated regions.

7. The method of claim 6, wherein said velocity profile further comprises velocity versus time information over a cardiac cycle, for each of said plurality of designated regions.

8. The method of claim 7, wherein said last to contract information from said plurality of designated regions is identified by determining which of said plurality of designated regions is last to attain a maximum velocity thereof.

9. The method of claim 1, wherein said determining a movement profile further comprises determining a contraction profile for the right ventricle (RV).

10. The method of claim 1, wherein:
the cardiac acquisition data is obtained from a computed tomography medical imaging system.

11. A method for planning biventricular pacing lead placement for a patient, the method comprising:
obtaining cardiac acquisition data from a medical imaging system;

determining a movement profile from said cardiac acquisition data, said movement profile directed toward identifying at least one of: a time-based contraction parameter for a region of the left ventricle (LV), and a displacement-based contraction parameter for a region of the LV;

visually displaying said determined movement profile by generating a 3D model therefrom;

visualizing one or more coronary vessels on said generated 3D model;

identifying at least one suitable region on the left ventricle wall for epicardial lead placement based on said determined movement profile and said visualized coronary vessels;

determining LV anatomical landmarks of interest and inserting geometric markers into said 3D model thereat; and registering said 3D model having said geometric markers with an interventional medical system for real-time 3D visualization of the LV and interventional lead placement thereat.

12. The method of claim 11, further comprising identifying the presence of any necrosed tissue and visualizing any of said necrosed tissue on said 3D model, wherein the identification of any sites of such necrosed tissue is used to eliminate said sites from epicardial lead placement.

13. The method of claim 11, wherein said identifying at least one suitable region further includes identifying the blood vessels on the epicardium of the left ventricle and eliminating at least one of the blood vessels and the myocardium directly under the blood vessels as a suitable region.

14. The method of claim 11, wherein said displacement-based contraction parameter further comprises a displacement profile for each of a plurality of designated regions.

15. The method of claim 14, wherein said displacement profile for each of a plurality of designated regions is used to identify one of said plurality of designated regions having a maximum displacement with respect to a starting position thereof at a given cardiac cycle point.

16. The method of claim 11, wherein said time-based contraction parameter further comprises last to contract information based upon displacement versus time information over a cardiac cycle, for each of a plurality of designated regions.

17. The method of claim 16, wherein a last to contract region from said plurality of designated regions is identified by determining which of said plurality of designated regions is last to attain a maximum displacement thereof.

18. The method of claim 11, wherein said time-based contraction parameter further comprises last to contract information based upon a velocity profile for each of a plurality of designated regions.

19. The method of claim 18, wherein said velocity profile further comprises velocity versus time information over a cardiac cycle, for each of said plurality of designated regions.

20. The method of claim 19, wherein said last to contract information from said plurality of designated regions is identified by determining which of said plurality of designated regions is last to attain a maximum velocity thereof.

21. The method of claim 11, wherein said identifying at least one suitable region further comprises quantifying selected dimensions of said blood vessels on the epicardium of the left ventricle.

22. The method of claim 11, wherein said determining a movement profile further comprises determining a contraction profile for the right ventricle (RV).

23. A method for planning biventricular pacing lead placement for a patient, the method comprising:
obtaining cardiac acquisition data from a medical imaging system;

determining a movement profile from said cardiac acquisition data, said movement profile directed toward identifying at least one of: a time-based contraction parameter for a region of the left ventricle (LV), and a displacement-based contraction parameter for a region of the LV;

visually displaying said determined movement profile by generating a 3D model therefrom;

visualizing one or more coronary vessels on said generated 3D model;

identifying at least one suitable region on the left ventricle wall for epicardial lead placement based on said determined movement profile and said visualized coronary vessels;

identifying coronary sinus branches closest to said at least one suitable region and displaying said identified coronary sinus branches on said 3D model;

identifying one or more left ventricle anatomical landmarks on said 3D model and inserting geometric markers into said 3D model thereat;

registering saved views of said 3D model having said inserted geometric markers on an interventional system;

visualizing one or more of said registered saved views with said interventional system; and identifying a minimally invasive route for epicardial lead placement at said at least one suitable region on the left ventricle wall based on said determined movement profile and said 3D model.

24. The method of claim 23, further comprising identifying the presence of any necrosed tissue and visualizing any of said necrosed tissue on said 3D model, wherein the identification of any sites of such necrosed tissue is used to eliminate said sites from epicardial lead placement.

25. The method of claim 21, wherein said identifying at least one suitable region further includes identifying the blood vessels on the epicardium of the left ventricle and eliminating at least one of the blood vessels and the myocardium directly under the blood vessels as a suitable region.

26. The method of claim 21, wherein said displacement-based contraction parameter further comprises a displacement profile for each of a plurality of designated regions.

27. The method of claim 26, wherein said displacement profile for each of a plurality of designated regions is used to identify one of said plurality of designated regions having a maximum displacement with respect to a starting position thereof at a given cardiac cycle point.

28. The method of claim 21, wherein said time-based contraction parameter further comprises last to contract information based upon displacement versus time information over a cardiac cycle, for each of a plurality of designated regions.

29. The method of claim 28, wherein a last to contract region from said plurality of designated regions is identified by determining which of said plurality of designated regions is last to attain a maximum displacement thereof.

30. The method of claim 23, wherein said time-based contraction parameter further comprises last to contract information based upon a velocity profile for each of a plurality of designated regions.

31. The method of claim 30, wherein said velocity profile further comprises velocity versus time information over a cardiac cycle, for each of said plurality of designated regions.

32. The method of claim 31, wherein said last to contract information from said plurality of designated regions is identified by determining which of said plurality of designated regions is last to attain a maximum velocity thereof.

33. The method of claim 23, further comprising utilizing post processing software to process said acquisition data so as to generate short axis images of the LV and thoracic wall.

34. The method of claim 33, wherein said 3D model and said short axis images are visualized through a display screen associated with said interventional system.

35. The method of claim 33, wherein said obtaining acquisition data is EKG gated.

36. The method of claim 33, further comprising segmenting said acquisition data using a 3D protocol and short axis protocols so as to visualize the thoracic wall, LV walls and epicardial fat.

37. The method of claim 33, wherein said medical imaging system is one of a computed tomography system, a magnetic resonance imaging system, an ultrasound system, and a 3D fluoroscopy system.

38. The method of claim 23, wherein said identifying at least one suitable region further comprises quantifying selected dimensions of said blood vessels on the epicardium of the left ventricle.

39. The method of claim 23, wherein said determining a movement profile further comprises determining a contraction profile for the right ventricle (RV).

40. The method of claim 23, further comprising generating, from said saved view of said 3D model, reports for diagnosis and interventional planning.

41. The method of claim 23, further comprising:
inserting geometric markers at the one or more anatomical landmarks such that the visualizing comprises visualizing the LV in a translucent fashion with opaque geometric markers.

42. A system for quantifying cardiac desynchrony of the right and left ventricles, comprising:
a medical imaging system for obtaining cardiac acquisition data;
an image generation subsystem configured to
(a) receive said acquisition data
(b) determine a movement profile from said cardiac acquisition data, and
(c) calculate at least one of the following from said movement profile: a time-based contraction parameter for a region of the left ventricle (LV), and a displacement-based contraction parameter for a region of the LV; and
an operator console configured to visually display said determined movement profile by generating a 3D model of the right and left ventricles therefrom;
wherein said operator console is configured for signal communication with an interventional system configured for identifying the presence of any necrosed tissue and for identifying a minimally invasive route for epicardial lead placement at said at least one suitable region on the left ventricle wall; and
wherein said operator console is configured for visualizing any of said necrosed tissue on said 3D model, wherein the identification of any sites of such necrosed tissue is used to eliminate said sites from the epicardial lead placement.

43. The system of claim 42, wherein said displacement-based contraction parameter further comprises a displacement profile for each of a plurality of designated regions.

44. The system of claim 43, wherein said displacement profile for each of a plurality of designated regions is used to identify one of said plurality of designated regions having a maximum displacement with respect to a starting position thereof at a given cardiac cycle point.

45. The system of claim 42, wherein said time-based contraction parameter further comprises last to contract information based upon displacement versus time information over a cardiac cycle, for each of a plurality of designated regions.

46. The system of claim 45, wherein a last to contract region from said plurality of designated regions is identified by determining which of said plurality of designated regions is last to attain a maximum displacement thereof.

47. The system of claim 42, wherein said time-based contraction parameter further comprises last to contract information based upon a velocity profile for each of a plurality of designated regions.

48. The system of claim 47, wherein said velocity profile further comprises velocity versus time information over a cardiac cycle, for each of said plurality of designated regions.

49. The system of claim 48, wherein said last to contract information from said plurality of designated regions is identified by determining which of said plurality of designated regions is last to attain a maximum velocity thereof.

50. The system of claim 42, wherein said a movement profile further comprises a contraction profile for the right ventricle (RV).

51. A system for planning biventricular pacing lead placement for a patient, comprising:
a computed tomography medical imaging system for generating acquisition data;
an image generation subsystem for receiving said acquisition data and determining a movement profile from said cardiac acquisition data, said movement profile directed toward identifying at least one of: a time-based contraction parameter for a region of the left ventricle (LV), and a displacement-based contraction parameter for a region of the LV;
an operator console for visually displaying said determined movement profile by generating a 3D model therefrom, said operator console further configured for visualizing one or more coronary vessels on said generated 3D model; and
a workstation including post processing software for registering saved views of said 3D model on an interventional system;
wherein said interventional system is configured for visualizing one or more of said registered saved views therewith and for identifying a minimally invasive route for epicardial lead placement at said at least one suitable region on the left ventricle wall.

52. The system of claim 51, wherein said workstation is configured for identifying the presence of any necrosed tissue, and said operator console is configured for visualizing any of said necrosed tissue on said 3D model, wherein the identification of any sites of such necrosed tissue is used to eliminate said sites from epicardial lead placement.

53. The system of claim 52, wherein said post processing software is further configured to process said acquisition data so as to generate short axis images of the LV and thoracic wall.

54. The system of claim 53, further comprising a display screen associated with said interventional system, said display screen for visualizing said 3D model and said short axis images.

55. The system of claim 51, wherein said image generating subsystem is EKG gated.

56. The system of claim 51, wherein said displacement-based contraction parameter further comprises a displacement profile for each of a plurality of designated regions.

57. The system of claim 56, wherein said displacement profile for each of a plurality of designated regions is used to identify one of said plurality of designated regions having a maximum displacement with respect to a starting position thereof at a given cardiac cycle point.

58. The system of claim 51, wherein said time-based contraction parameter further comprises last to contract information based upon displacement versus time information over a cardiac cycle, for each of a plurality of designated regions.

59. The system of claim 58, wherein a last to contract region from said plurality of designated regions is identified by determining which of said plurality of designated regions is last to attain a maximum displacement thereof.

60. The system of claim 51, wherein said time-based contraction parameter further comprises last to contract information based upon a velocity profile for each of a plurality of designated regions.

61. The system of claim 60, wherein said velocity profile further comprises velocity versus time information over a cardiac cycle, for each of said plurality of designated regions.

62. The system of claim 61, wherein said last to contract information from said plurality of designated regions is identified by determining which of said plurality of designated regions is last to attain a maximum velocity thereof.

63. The system of claim 51, wherein said medical imaging system is one of a computed tomography system, a magnetic resonance imaging system, an ultrasound system, and a 3D fluoroscopy system.

64. The system of claim 51, wherein operator console is further configured for quantifying selected dimensions of said blood vessels on the epicardium of the left ventricle.

65. The system of claim 51, wherein said movement profile further comprises a contraction profile for the right ventricle (RV).

66. The system of claim 51, wherein said workstation is further configured for generating, from said saved view of said 3D model, reports for diagnosis and interventional planning.

67. The system of claim 51, wherein:
the workstation is configured for inserting geometric markers at one or more left ventricle anatomical landmarks corresponding to the 3D model.

68. The system of claim 67, wherein:
the workstation is configured to display the left ventricle in a translucent fashion and the geometric markers in an opaque fashion.

* * * * *